(12) United States Patent
Street et al.

(10) Patent No.: US 8,703,050 B2
(45) Date of Patent: Apr. 22, 2014

(54) COMPOSITION FOR PHOTODYNAMIC DISINFECTION

(75) Inventors: Cale Street, Edmonds, WA (US); Lisa Pedigo, Lake Forest Park, WA (US); Nicolas Loebel, Woodinville, WA (US)

(73) Assignee: Ondine International Ltd., St. Michael (BB)

( * ) Notice: Subject to any disclaimer, the term of this patent is extended or adjusted under 35 U.S.C. 154(b) by 518 days.

(21) Appl. No.: 12/603,861

(22) Filed: Oct. 22, 2009

(65) Prior Publication Data
US 2010/0233022 A1 Sep. 16, 2010

Related U.S. Application Data

(60) Provisional application No. 61/160,435, filed on Mar. 16, 2009.

(30) Foreign Application Priority Data

Oct. 21, 2009 (WO) ................ PCT/US2009/061442

(51) Int. Cl.
*A61L 9/01* (2006.01)
*B01J 19/08* (2006.01)
*A61N 5/00* (2006.01)
*C12N 13/00* (2006.01)

(52) U.S. Cl.
USPC ...... 422/24; 422/1; 422/22; 422/28; 422/186; 250/492.1; 134/1; 424/76.8; 435/173.1

(58) Field of Classification Search
USPC ............. 422/1, 22, 24, 28, 186, 186.3, 292; 250/455.11, 492.1; 134/1, 26, 95.3; 424/76.8; 435/173.1, 292.1
See application file for complete search history.

(56) References Cited

U.S. PATENT DOCUMENTS

| | | | |
|---|---|---|---|
| 5,179,120 A | 1/1993 | Vogel et al. | |
| 5,611,793 A | 3/1997 | Wilson et al. | |
| 6,693,093 B2 | 2/2004 | Chowdhary et al. | |
| 2004/0121019 A1* | 6/2004 | Perrier et al. | 424/490 |
| 2006/0223729 A1* | 10/2006 | Hamblin et al. | 510/130 |
| 2008/0255498 A1* | 10/2008 | Houle | 604/20 |

FOREIGN PATENT DOCUMENTS

| | | |
|---|---|---|
| WO | 2008109424 A | 9/2008 |
| WO | 2009018205 A | 2/2009 |

OTHER PUBLICATIONS

J, R, Furr and A. D. Russell, Factors influencing the activity of esters of p-hydroxybenzoic acid on *Serratia marcescens*, *Microbios*, 1972.
E. Freese, C. W. Sheu and E. Galliers, Function of lipophilic acids as antimicrobial food additives, *Nature*, 1973, 241:321-325.

(Continued)

*Primary Examiner* — Monzer R Chorbaji
(74) *Attorney, Agent, or Firm* — The Dobrusin Law Firm, PC

(57) ABSTRACT

The present invention includes a composition for enhancing the antimicrobial efficacy of photodynamic disinfection against Gram-negative organism that is receptive to paraben potentiation using a composition comprising a photosensitizer and at least one paraben. The present invention also includes a method for photodynamic disinfection comprising applying the composition to a desired treatment area and applying light to the desired treatment area at a wavelength absorbed by the photosensitizer so as to inhibit Gram-negative organism located within the treatment area wherein the Gram-negative organism is receptive to paraben potentiation.

13 Claims, 1 Drawing Sheet

(56) References Cited

OTHER PUBLICATIONS

T. J. Eklund, The effect of sorbic acid and esters of p-hydroxybenzoic acid on the protonmotive force in *Escherichia coli* membrane vesicles, *Gen Microbiol* 1985, 131:73-6.

L. Panicker, Effect of propyl paraben on the dipalmitoyl phosphatidic acid vesicles, *J Colloid Interface Science*, 2007, 311:407-416.

J. Breslin: A. Davin-Regli and J. M. Pages, Propyl paraben induces potassium efflux in *Escherichia coli, J Antimicrobial Chemo.* 2005, 55:1013-1015.

T. Nguyen, B. Clare, W. Guo and B. Martinac, The effects of parabens on the mechanosensitive channels of *E. coli, Eur Biophys J.*, 2005, 34(5):389-95.

Y. Ma, and R. E. Marquis, Irreversible paraben inhibition of glycolysis by *Streptococcus mutans* GS-5, *Lett Appl Microbiol*, 1996, 23:329-33.

Meyer Brian K et al: "Antimicrobial preservative use in parenteral products: past and present" Journal of Pharmaceutical Sciences, American Pharmaceutical Association, Washington, US, vol. 96, No. 12, Jan. 1, 2007, pp. 3155-3167, XP009099142 ISSN:0022-3549 table 1.

Wainwright M et al: "A Study of Photobactericidal Activity in the Phenothiazinium Series" Fems Immunology and Medical Microbiology, Elsevier Science B.V., Amsterdam, NL, vol. 19, No. 1, Sep. 1, 1997, pp. 75-80, XP001042388 ISSN:0928-8244.

\* cited by examiner

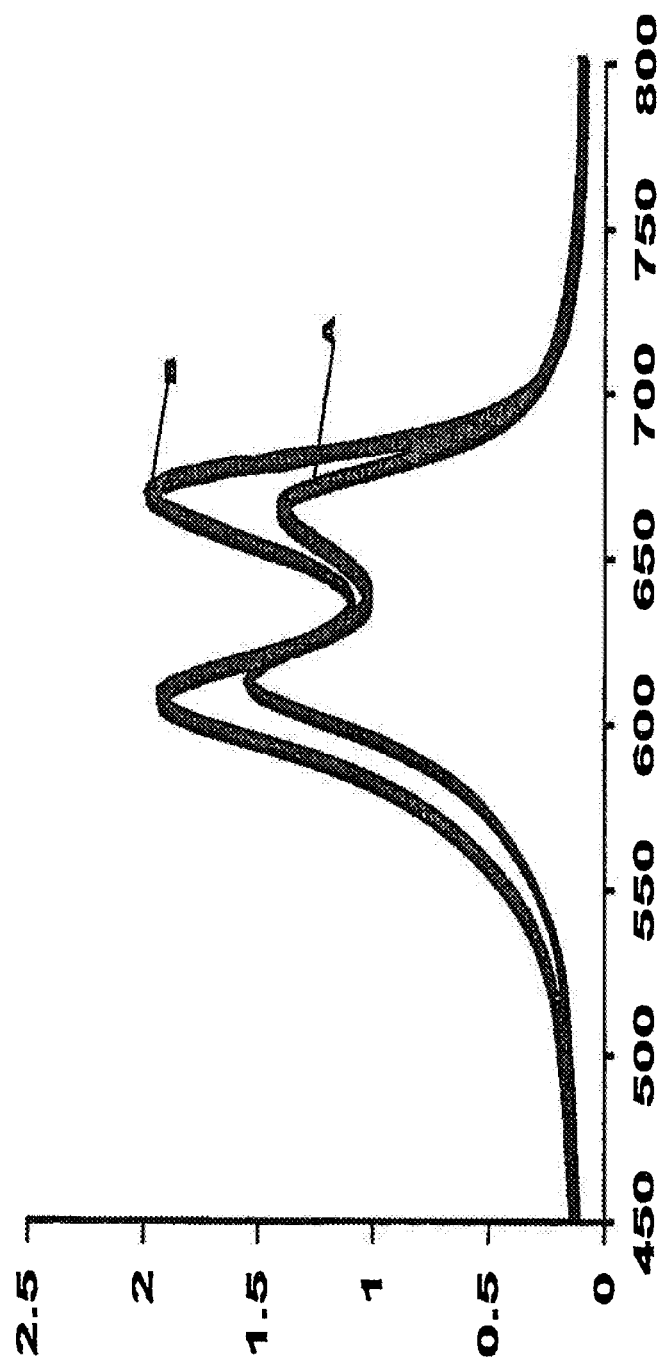

COMPOSITION FOR PHOTODYNAMIC DISINFECTION

CLAIM OF BENEFIT OF FILING DATE

This application claims the benefit of the filing date of U.S. Provisional Application Ser. No. 61/160,435 titled: "COMPOSITION AND METHOD FOR PHOTODYNAMIC DISINFECTION" filed on Mar. 16, 2009, and PCT Patent Application No. PCT/US09/61442 titled: "COMPOSITION AND METHOD FOR PHOTODYNAMIC DISINFECTION" filed on Oct. 21, 2009; both applications incorporated herein by reference for all purposes.

FIELD OF THE INVENTION

The present invention relates to a photosensitizer composition useful for photodynamic disinfection of Gram-negative organisms. More particularly, the present invention relates to a photosensitizer composition that when used for photodynamic disinfection has significantly enhanced antimicrobial efficacy against specific Gram-negative organisms due to a synergistic antimicrobial effect between the photosensitizer and one or more paraben.

BACKGROUND OF THE INVENTION

Photodynamic Disinfection (PDD) has been demonstrated to be an effective non-antibiotic antimicrobial approach in vitro. One exemplary advantage of PDD as an antimicrobial treatment modality is that, due to its non-specific bactericidal mechanism, it is typically not subject to issues of resistance that can plague the use of antibiotics. As another exemplary advantage, it can be employed as a localized topical treatment that can be administered in areas such as the oral or nasal cavities where sustained topical antibiotic delivery can be problematic. For these reasons and others, PDD is fast becoming a valuable tool in the treatment of bacterial-related conditions such as periodontal disease.

PDD fundamentally involves the use of light energy to activate one or more photosensitizers of a photosensitizer composition so that those photosensitizers can then either interact directly with a substrate/target (type I reaction), or can interact with molecular oxygen to produce singlet oxygen and other reactive oxygen species (type II reaction). These reactions mediate the non-specific killing of microbial cells primarily via lipid peroxidation, membrane damage, and damage to intracellular components. In order for this process to kill and/or reduce microbes, it is typically desirable that the photosensitizer be internalized into or brought into very close association with the cellular envelope of such microbes.

The esters of p-hydroxybenzoic acid, commonly referred to as parabens, are among the most commonly used preservatives in cosmetic and pharmaceutical formulations. They offer the advantages of broad antimicrobial activity, efficacy over a wide pH range, low toxicity, and low sensitization potential. In addition, these compounds are relatively odorless, colorless and highly stable. Parabens are typically most effective against fungi and Gram positive bacteria. Combinations of parabens such as methylparaben (methyl-4-hydroxybenzoate) and propylparaben (propyl-4-hydroxybenzoate) offer greater preservative activity and improved solubility over individual parabens, and these combinations are commonly used in commercial products.

The mechanisms of antimicrobial action of parabens are just beginning to be fully understood, and evidence for several processes has been proposed. Furr and Russell detected intracellular leakage of RNA when *Serratia marcescens* was exposed to parabens indicating disruption of cellular membrane transport processes (see J. R. Furr and A. D. Russell, Factors influencing the activity of esters of p-hydroxybenzoic acid on *Serratia marcescens*, *Microbios*, 1972). Freese, et al. determined that parabens interfered with both membrane transport and electron transport systems (see E. Freese, C. W. Sheu and E. Galliers, Function of lipophilic acids as antimicrobial food additives, *Nature*, 1973, 241:321-325).

Eklund found that parabens eliminated the change in pH of the cytoplasmic membrane, but did not disrupt the membrane potential component of the proton motive force. He subsequently concluded that neutralization of the proton motive force and subsequent transport inhibition could not be the only mechanism of inhibition (see T. J. Eklund, The effect of sorbic acid and esters of p-hydroxybenzoic acid on the protonmotive force in *Escherichia coli* membrane vesicles, *Gen Microbiol* 1985, 131:73-6).

Work by Panicker with dipalmitoyl phosphatidic acid vesicles, a membrane system model, revealed a concentration dependent interaction of propylparaben with the lipid membrane. At low concentrations propylparaben altered membrane function by interacting with the cell wall allowing passive transmembrane diffusion to the target receptor. At high concentrations, propylparaben interacted with lipid components making the cell wall more rigid. This in turn altered membrane semipermeability and thus membrane function (see L. Panicker, Effect of propyl paraben on the dipalmitoyl phosphatidic acid vesicles, *J Colloid Interface Science*, 2007, 311:407-416).

Bredin, et al. reported that membrane destabilization was induced when *E. coli* was exposed to propylparaben. Upon exposure, potassium was released in a manner similar to polymyxin B induction of outer membrane permeabilization. Furthermore, this efflux was dependent upon porin channel activity (see J. Bredin, A. Davin-Regli and J. M. Pages, Propyl paraben induces potassium efflux in *Escherichia coli*, *J Antimicrobial Chemo.* 2005, 55:1013-1015).

Nguyen, et al. showed that ethyl- and propylparaben interacted with the mechanosensitive channels of large and small conductance thereby disrupting osmotic gradients in *E. coli* (see T. Nguyen, B. Clare, W. Guo and B. Martinac, The effects of parabens on the mechanosensitive channels of *E. coli*, *Eur Biophys J.*, 2005, 34(5):389-95).

Finally, in addition to membrane disruptive mechanisms, Ma, et al. showed that parabens were highly effective inhibitors of bacterial enzyme systems. For example, F-ATPases were reversibly inhibited in *Streptococcus mutans*, but the membrane protein (Enzyme II) of the phosphopyruvate:phosphotransferase system for glucose uptake and phosphorylation was irreversible inhibited (see Y. Ma, and R. E. Marquis, Irreversible paraben inhibition of glycolysis by *Streptococcus mutans* GS-5, *Lett Appl Microbiol*, 1996, 23:329-33).

SUMMARY OF THE INVENTION

The present invention provides a composition comprising a photosensitizer and at least one paraben to provide a synergistic antimicrobial effect against specific Gram-negative organisms. This synergistic antimicrobial effect against specific Gram-negative organisms, hereinafter be referred to as "paraben potentiation", is defined and discussed below in this specification. It is preferred that the composition further includes a pharmaceutically acceptable carrier.

The present invention also provides a method for photodynamic disinfection comprising: applying the composition comprising a photosensitizer and at least one paraben to Gram-negative organism located within a desired treatment area wherein the Gram-negative organism is receptive to paraben potentiation; and applying light to the treatment area at a wavelength absorbed by the photosensitizer so as to eliminate the Gram-negative organism.

BRIEF DESCRIPTION OF THE DRAWINGS

The features and inventive aspects of the present invention will become more apparent upon reading the following detailed description, claims, and drawings, of which the following is a brief description:

FIG. 1 is a graph showing the absorbance profile of two compositions described below in Example I.

DETAILED DESCRIPTION OF THE INVENTION

The composition of the present invention includes a photosensitizer and at least one paraben. The composition is preferred to further include a pharmaceutically acceptable carrier. As shown below in Examples below, the composition has greater antimicrobial efficacy against specific Gram-negative organism as compared to the sum total of antimicrobial efficacy against the same Gram-negative organism using photodynamic disinfection (under similar or even identical parameters) and paraben(s) alone. This greater antimicrobial efficacy against such specific Gram-negative organism shall hereinafter be referred to as "paraben potentiation".

The photosensitizer can be any suitable art-disclosed photosensitizer. For example, the photosensitizer can be a phenothiazinium salt (e.g., methylene blue, toluidine blue O and their derivatives, etc.). Arianor steel blue, crystal violet, azure blue cert, azure B chloride, azure 2, azure A chloride, azure B tetrafluoroborate, thionin, azure A eosinate, azure B eosinate, azure mix sicc., azure II eosinate, haematoporphyrin HCl, haematoporphyrin ester, aluminium disulphonated phthalocyanine are examples of suitable photosensitizers. Porphyrins, pyrroles, tetrapyrrolic compounds, expanded pyrrolic macrocycles, and their respective derivatives are further examples of suitable photosensitizers. Photofrin® manufactured by QLT PhotoTherapeutics Inc., Vancouver, B.C., Canada is yet another example of a suitable photosensitizer. Other exemplary photosensitizers may be found in U.S. Pat. Nos. 5,611,793 and 6,693,093. The photosensitizers mentioned above are examples are not intended to limit the scope of the present invention in any way.

Depending on the desired application, the composition may optionally comprise a plurality of the photosensitizers. The amount or concentration of the photosensitizer(s) may vary depending upon the desired application, the particular photosensitizer(s) used, and the target Gram-negative organisms to be inhibited. The term inhibit and/or inhibited shall mean prevent, reduce, destroy, kill, eliminate, or the like. For example, concentration of the photosensitizer(s) in the composition may range from about 0.00001% w/v to about 25% w/v, from about 0.0001% w/v to about 10% w/v, from about 0.001% w/v to about 1% w/v, from about 0.001% w/v to about 0.1% w/v, from about 0.01% w/v to about 1% w/v, from about 0.005% w/v to about 0.05% w/v. The term "about" as used herein in this specification shall mean +/−20% of the stated value.

The at least one paraben can be any suitable art-disclosed paraben compound (also known as esters of p-hydroxybenzoic acid). For example, methylparaben (methyl-4-hydroxybenzoate), propylparaben (propyl-4-hydroxybenzoate), and a combination thereof. The amount or concentration of the paraben(s) may vary depending upon the desired application, the particular photosensitizer(s) used, and the target Gram-negative organisms to be inhibited. For example, concentration of the paraben(s) in the composition may range from about 0.00001% to about 25% w/v, from about 0.0001% to about 10% w/v, from about 0.001% to about 1% w/v, from about 0.01% w/v to about 0.1% w/v, from about 0.01% w/v to about 0.5% w/v and from about 0.005% w/v to about 0.05% w/v.

The pharmaceutically acceptable carrier is a diluent, adjuvant, excipient, or vehicle with which the other components (e.g., the photosensitizer and the at least one paraben, etc.) of the composition are administered. The pharmaceutically acceptable carrier is preferably approved by a regulatory agency of the Federal or a state government, or listed in the U.S. Pharmacopeia or other generally recognized pharmacopeia for use in animals, and more particularly in humans. Examples of the pharmaceutically acceptable carriers include but are not limited to water, saline solution, dextrose solution, glycerol solution, phosphate buffered saline solution, etc.

The composition may optionally comprise addition components such as anti-inflammatory agents, buffers, salts for adjusting the tonicity of the solution, antioxidants, additional preservatives, viscosity-altering agents (e.g., carboxymethylcellulose, hydroxypropylmethylcellulose, hydroxypropylcellulose, etc.), flavoring/scent (e.g., sucralose, etc.), oxygen carrier molecules, cell permeabilizing agents, antibiotics, bactericides/bacteriostats or the like.

The present invention also provides a method for photodynamic disinfection comprising: applying the composition comprising a photosensitizer and at least one paraben to Gram-negative organism located within desired treatment area wherein the Gram-negative organism is receptive to paraben potentiation; and applying light to the desired treatment area at a wavelength absorbed by the photosensitizer so as to inhibit the Gram-negative organism. The desired treatment area can be any area where anti-microbial treatment is desired (e.g., around human tissue, animal tissue, another substrate or otherwise).

The term "Gram-negative organism is receptive to paraben potentiation" shall mean Gram-negative organism(s) that when subjected to photodynamic disinfection using the composition of the present invention would show paraben potentiation. Examples of Gram-negative organism that is receptive to paraben potentiation include, but are not limited to, *Escherichia coli* ("*E. coli*"), *Pseudomonas aeruginosa*, *Acinetobacter* sp., and pathogenic Gram-negative organisms residing within the oral cavity (e.g., *Porphyromonas, Prevotella, Fusobacterium, Tannerella, Actinobacillus, Selenomonas, Eikenella, Campylobacter, Wolinella*, etc.). *Porphyromonas gingivalis* and *Prevotella intermedia* are examples of such oral pathogenic Gram-negative organisms.

The wavelength can be any wavelength(s) of light that can be absorbed by the photosensitizer(s) of the composition. The wavelengths include wavelengths selected from the continuous electromagnetic spectrum such as ultraviolet ("UV"), visible, the infrared (near, mid and far), etc. For examples, the wavelengths are between about 160 nm to about 1600 nm, between 400 nm to about 800 nm, between about 500 nm to about 850 nm, between about 600 nm to about 700 nm although the wavelengths may vary depending upon the particular photosensitizer(s) used and the light intensity. The light may be produced by any suitable art-disclosed light emitting devices for use in photodynamic disinfection such as lasers (e.g., non-thermal lasers or the like), light emitting diodes ("LEDs"), incandescent sources, fluorescent sources, or the like.

Depending on the photosensitizer concentration and the power of the light emitting device(s), the application of light to the treatment site may only require a short period of time such as from about 15 seconds to less than about 5 minutes, preferably from about 15 seconds to about two minutes, more preferably for about 15 seconds to about 90 seconds, and most preferably for about 30 seconds to 60 seconds. The light energy provided during each cycle of application of light may range from about 1 $J/cm^2$ to about 50 $J/cm^2$, from about 1 $J/cm^2$ to about 25 $J/cm^2$, from about 5 $J/cm^2$ to about 20 $J/cm^2$, and from at about 6 $J/cm^2$ to about 12 $J/cm^2$. Depending on the nature and extent of the Gram-negative organism located at the treatment site, the practitioner may apply multiple cycles of light applications (e.g., about 2 to about 10, about 3 to about 5, etc.) to the treatment site thereby resulting in a total accumulated light energy applied to treatment site that can be substantially higher than the light energy provided during each cycle.

Again depending on the nature and extent of the Gram-negative organism located at the treatment site, the entire method can be repeated multiple times (e.g., about 2 to about 10, about 3 to about 5, etc.) until the desired effects have been reached. It is preferred that the selections of photosensitizer concentration, wavelength, and/or total accumulated light energy applied to treatment site will allow the method of the present invention to reduce over about 90%, more preferably over 95%, and most preferably over 99% of the target Gram-negative organism located at the treatment site. It is also preferred that the application of light to the treatment site does not cause physiological damage to the host tissues at and/or surround the treatment site.

The present invention is not being limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all numerical values are approximate and are provided for description only. Patents, patent applications, and publications cited throughout this application are incorporated herein by reference in their entireties.

The following example provided in accordance to the present invention is for illustrative purpose only and is not intended as being exhaustive or limiting of the invention.

Example I

Composition A had the active ingredient of about 0.01% w/v methylene blue in a phosphate buffered saline solution. Composition B was the same as Composition A except it also contained about 0.18% w/v methylparaben and about 0.02% w/v propylparaben.

Optical absorbance characteristics of Composition A and Composition B were examined spectrophotometrically using a custom designed 1 mm path length cuvette and the results are shown in FIG. 1. The vertical scale of FIG. 1 shows the optical density at 1 mm pathlength (i.e., absorbance). The horizontal scale of FIG. 1 shows the wavelength in nm. Line A in FIG. 1 represents the absorbance profile of Composition A. Line B of FIG. 1 represents the absorbance profile of Composition B.

An absorbance peak at 665-670 nm range indicates the presence of the monomeric form of methylene blue. A second peak at 600-610 nm indicates the presence of the dimerized form of methylene blue. It has been shown that the dimerized form of methylene blue is less effective at generating singlet oxygen; and therefore, it is believed to be less effective antimicrobially.

The characteristic absorbance profiles shown in FIG. 1 indicate that Composition A resulted in lower levels of the monomer form of methylene blue compared to Composition B. Composition B containing the parabens elevated the monomer absorbance peak of methylene blue. It appeared that the addition of parabens shifted the ratio of methylene blue monomer:dimer in favor of the monomeric form of methylene blue. As explained by Tardivo et al, methylene blue in non-aggregated (i.e. monomeric) form can be photochemically excited to high quantum yield triplet form, yielding singlet oxygen which is believed to be the primary toxic species in antimicrobial photodynamic disinfection. In contrast, aggregated (dimerized, trimerized, etc.) forms of methylene blue do not effect singlet oxygen generation, and are thus less useful from an antimicrobial perspective. Thus, in a methylene blue photosensitizer preparation designed for antimicrobial applications, it is desirable to have a high ratio of monomer to dimer (see Tardivo, J., Giglio, A., Oliveira, C., Gabrielli, D., Junqueira, H., Tada, D., Severino, D., Turchiello, R., Baptista, M., 2005. Methylene blue in photodynamic therapy: From basic mechanisms to clinical applications, *Photodiagnosis and Photodynamic Therapy*. v. 2, p. 175-191).

Example II

An in vitro experiment was conducted by applying a control containing a phosphate buffered saline solution and the following two compositions to planktonic *E. coli* (*Escherichia coli* ATCC® 25922™) cultures at approximately $10^7$ to $10^8$ colony forming units per milliliter ("CFU/ml"). Composition C contained the active ingredient of methylene blue at a concentration of about 0.01% w/v in an isotonic buffered vehicle preserved with sodium benzoate at a concentration of about 0.2% w/v. Composition D contained the active ingredient of methylene blue at a concentration of about 0.01% w/v, with methylparaben at a concentration of about 0.18% w/v, propylparaben at a concentration of about 0.02% w/v in an isotonic buffered vehicle. The isotonic buffered vehicle is comprised of a flavoring agent (e.g., sucralose) and a viscosity-altering agent (e.g., carboxymethylcellulose) in a phosphate buffered saline solution. The phosphate buffered saline only control and the above described compositions were at about neutral pH (e.g., about pH 7).

Planktonic *E. coli* cultures exposed to either Composition C or Composition D were irradiated using a laser with a power output of about 220 mW at a wavelength of about 670 nm for durations of about 60 seconds at a power density of about 344 $mW/cm^2$ with an overall energy dose of about 20.6 $J/cm^2$. In addition, planktonic *E. coli* cultures exposed to either phosphate buffered saline, Composition C, or Composition D for 60 seconds without illumination were used as "no light" controls. After the above-described treatment(s), samples were serially diluted and plated on solid media for 24 hours (thereby allowing colonies of planktonic *E. coli* to become visible in the non-irradiated phosphate buffered saline only control ("Control"). Plate counts for replicates of each experimental condition were averaged and back-calculated taking dilution into account to give data in CFU/ml. The data was presented as CFU/ml of surviving organisms after treatment, and rate of reduction of planktonic *E. coli*'s viability ("kill rate") was calculated as this value in experimental samples vs. the Control and expressed as both a $\log_{10}$ and percentage reduction in planktonic *E. coli*'s viability ("PE viability"). The results showed significantly greater antimicrobial efficacy after exposure to the irradiated Composition D as compared to irradiated Composition C. The irradiated Composition D achieved total eradication (>7.2 $\log_{10}$ reduction in PE viability) of planktonic *E. coli*, as opposed to the irradiated Composition C which only achieved a 3.1 $\log_{10}$ reduction in PE viability. This difference in kill rate was statistically significant (p<0.05). Exposure to non-irradiated Composition D resulted in no observable decrease in PE viability, indicating that the parabens at that concentration exhibited no acute antimicrobial effects on their own. These results were unexpected and showed that the combination of a photosensitizer (e.g., a phenothiazine such as methylene blue) and paraben(s) provided paraben potentiation and delivered greater antimicrobial efficacy against planktonic *E. Coli* when used during photodynamic disinfection.

Example III

Another in vitro study was conducted by applying a control containing the same phosphate buffered saline solution as described in Example II and the following four photosensitizer compositions to planktonic *E. coli* (*Escherichia coli* ATCC® 25922™) cultures at approximately $10^7$ to $10^8$ CFU/ml. Composition E contained the isotonic buffered vehicle as described in Example II with the following active ingredients: methylene blue at a concentration of about 0.01% w/v. Composition F is the same as Composition E with the addition of methylparaben at a concentration of about 0.18% w/v. Composition G is the same as Composition E with the addition of propylparaben at a concentration of about 0.02% w/v. Composition H is same as Composition E with the addition of methylparaben at a concentration of about 0.18% w/v and propylparaben at a concentration of about 0.02% w/v. All of the compositions were at a neutral pH level (e.g., about 7 pH).

The planktonic *E. coli* cultures exposed to the four above-described compositions (Composition E, F, G and H) were irradiated using a laser with a power output of about 220 mW at a wavelength of about 670 nm for durations of about 60 seconds at a power density of about 344 mW/cm$^2$ with an overall energy dose of about 20.6 J/cm$^2$. After the above-described treatment(s), samples were serially diluted and plated on solid media for 24 hours (thereby allowing colonies of planktonic *E. coli* to become visible in the Control. Plate counts for replicates of each experimental condition were averaged and back-calculated taking dilution into account to give data in CFU/ml. The data was presented as CFU/ml of surviving organisms after treatment(s), and kill rate was calculated as this value in experimental samples vs. the Control and expressed as both a $\log_{10}$ and percentage reduction in planktonic *E. coli*'s viability.

The data showed that the irradiated photosensitizer compositions containing about 0.18% w/v methylparaben alone or in combination with about 0.02% w/v propylparaben (Composition F and Composition H) achieved total eradication of *E. coli* (i.e., >7.9 $\log_{10}$ reduction in PE viability). Irradiated Composition G (containing about 0.02% w/v propylparaben) achieved a 7.0 $\log_{10}$ reduction in PE viability. Irradiated Composition E, containing no parabens, showed significantly less antimicrobial efficacy with a 3.9 $\log_{10}$ reduction in PE viability.

The results of this study further indicated that the addition of paraben(s) to a photosensitizer composition results in paraben potentiation when used in photodynamic disinfection of a Gram-negative organism.

Example IV

An in vitro study was conducted by exposing planktonic *E. coli* (*Escherichia coli* ATCC® 25922™) cultures at approximately $10^7$ to $10^8$ CFU/ml to eight photosensitizer compositions. Methylene blue at a concentration of about 0.01% w/v in the isotonic buffered vehicle as described in Example II was adjusted to pH levels of about 5, 6, 7 and 8 respectively, resulting in Composition I at about pH 5, Composition J at about pH 6, Composition K at about pH 7, and Composition L at about pH 8. Composition M (at about pH 5), Composition N (at about pH 6), Composition O (at about pH 7) and Composition P (at about pH 8) had the following ingredients: methylene blue at a concentration of about 0.01% w/v, methylparaben at a concentration of about 0.18% w/v, propylparaben at a concentration of about 0.02% w/v, in the same isotonic buffered vehicle as described in Example II.

After exposure of planktonic *E. coli* cultures to the eight above-described compositions, irradiation was performed using a laser with a power output of about 220 mW at a wavelength of about 670 nm for durations of about 60 seconds at a power density of about 344 mW/cm$^2$ with an overall energy dose of about 20.6 J/cm$^2$. After the above-described treatment(s), samples were serially diluted and plated on solid media for 24 hours (thereby allowing colonies of planktonic *E. coli* to become visible in the Control. Plate counts for replicates of each experimental condition were averaged and back-calculated taking dilution into account to give data in CFU/ml. The data was presented as CFU/ml of surviving organisms after treatment(s), and kill rate was calculated as this value in experimental samples vs. the Control and expressed as both a $\log_{10}$ and percentage reduction in planktonic *E. coli*'s viability.

Irradiated Composition I resulted in a 2.7 $\log_{10}$ reduction in PE viability, while irradiated Composition M at the same pH level of about 5 had gave a 3.4 $\log_{10}$ reduction in PE viability. Irradiated composition J achieved a 4.3 $\log_{10}$ reduction in PE viability while irradiated Composition N at the same pH level of about 6 achieved a 5.4 $\log_{10}$ reduction in PE viability. Irradiated Composition K achieved a 4.7 $\log_{10}$ reduction in PE viability, while irradiated Composition O at the same pH level of about 7 resulted in total eradication (>7.9 $\log_{10}$ reduction in PE viability). Finally, exposure to irradiated Composition L resulted in a 4.8 $\log_{10}$ reduction in PE viability, while exposure to irradiated Composition P at the same pH level of about 8 resulted in total eradication (>7.9 $\log_{10}$ reduction in PE viability).

The data showed that irradiated photosensitizer compositions containing parabens (Composition M, N, O and P) had better antimicrobial efficacy at all of the pH levels tested compared to the identical photosensitizer compositions containing no parabens (Composition I, J, K and L). Furthermore, an overall increase in antimicrobial efficacy with increasing pH levels were observed for both the photosensitizer compositions containing parabens and the compositions containing no parabens.

Example V

Another in vitro study was conducted by applying a control containing a phosphate buffered saline solution and three photosensitizer compositions to each of the following planktonic bacterial cultures: *Escherichia coli* ATCC® 25922™ (Gram-negative), *Pseudomonas aeruginosa* ATCC® 9027™ (Gram-negative), *Serratia marcescens* ATCC® 43862™ (Gram-negative), *Staphylococcus aureus* subsp. *aureus* ATCC® 25923™ (Methicillin sensitive and Gram-positive) and *Staphylococcus epidermidis* ATCC® 49461™ (Gram-positive) cultures at approximately $10^6$ to $10^7$ CFU/ml. Composition Q contained the following ingredients: methylene blue at a concentration of about 0.01% w/v, in the isotonic buffered vehicle as described in Example II. Composition R contained the same ingredients as Composition Q with the addition of methylparaben at a concentration of about 0.18% w/v and propylparaben at a concentration of about 0.02% w/v. Composition S contained methylene blue at a concentration of about 0.01% w/v, in the isotonic buffered vehicle as described in Example II preserved with sodium benzoate at a concentration of about 0.2% w/v. All of the compositions were at a neutral pH level (e.g., about 7 pH).

After exposure to one of the above-described compositions (Composition Q, R and S), each bacterial culture was irradiated using a laser with a power output of about 220 mW at a wavelength of about 670 nm for durations of about 60 seconds at a power density of about 344 mW/cm$^2$ with an overall energy dose of about 20.6 J/cm$^2$. After the above-described treatment(s), samples were serially diluted and plated on solid media for 24 hours (thereby allowing colonies of bacteria to become visible in the non-irradiated phosphate buffered saline only controls). Plate counts for replicates of each experimental condition were averaged and back-calculated taking dilution into account to give data in CFU/ml. The data was presented as CFU/ml of surviving organisms after treatment(s), and kill rate was calculated as this value in experimental samples vs. the applicable non-irradiated phosphate buffered saline only control and expressed as both a $\log_{10}$ and percentage reduction in bacterial viability ("B. viability").

This experiment examined the antimicrobial efficacy of photosensitizer compositions with and without parabens used for photodynamic disinfection against Gram-negative and Gram-positive organisms. For *E. coli*, the compositions without parabens (Composition Q and S) both effected a 3.9 $\log_{10}$ reduction in B. viability, while the irradiated composition with parabens (Composition R) effected a 5.6 $\log_{10}$ reduction in B. viability. For *Pseudomonas aeruginosa*, the irradiated compositions without parabens (Composition Q and S) both achieved a 2.8 $\log_{10}$ reduction in B. viability, while the irradiated composition with parabens (Composition R) achieved a 6.6 $\log_{10}$ reduction in B. viability. For *Serratia marcescens*, irradiated composition Q without parabens achieved a 3.3 $\log_{10}$ reduction in B. viability and irradiated Composition S without parabens achieved a 4.1 $\log_{10}$ reduction in B. viability. For the same organism, the irradiated composition with parabens (Composition R) effected a 4.1 $\log_{10}$ reduction in B. viability. For *Staphylococcus aureus*, the irradiated compositions without parabens (Composition Q and S) both effected a 4.0 $\log_{10}$ reduction in B. viability, while the irradiated composition with parabens (Composition R) effected a 3.9 $\log_{10}$ reduction in B. viability. Finally, for *Staphylococcus epidermidis*, irradiated composition Q without parabens achieved a 3.4 $\log_{10}$ reduction in B. viability and irradiated Composition S without parabens achieved a 3.7 $\log_{10}$ reduction in B. viability. In the same strain, the irradiated composition with parabens (Composition R) achieved a 4.6 $\log_{10}$ reduction in B. viability.

The results of this study show that irradiated photosensitizer compositions containing parabens (Composition R) have greater antimicrobial efficacy against the Gram-negative strains *E. coli* and *Pseudomonas aeruginosa* as compared to the irradiated compositions that did not contain parabens (Composition Q and S). The third Gram-negative organism evaluated, *S. marcescens*, did not appear to be eradicated to a greater degree in paraben-containing compositions, indicating that this organism is not susceptible to paraben potentiation. In a previous study, Furr and Russell observed that methyl and ethyl parabens were not taken up by whole cells or isolated cell wall of *S. marcescens* however propyl and butyl paraben were. (see J. R. Furr and A. D. Russell, Factors influencing the activity of esters of p-hydroxybenzoic acid on *Serratia marcescens, Microbios,* 1972). The two Gram-positive organisms evaluated, *S. aureus* and *S. epidermidis*, were also not susceptible to paraben potentiation and were eradicated to the same degree after exposure to paraben and non-paraben irradiated compositions. Taken together, these results suggest that parabens potentiate the antimicrobial efficacy of photodynamic disinfection against certain Gram-negative organisms (i.e., Gram-negative organisms that are receptive to paraben potentiation), and the paraben potentiation effect is greatest when the pH is approximately neutral or higher.

Since parabens cause permeability changes in the bacterial membrane, it is believed that this may have facilitated an increased penetration of photosensitizer into the cells of Gram-negative organisms. These changes might also have allowed an increased association of methylene blue molecules with the Gram-negative bacterial membrane (i.e. lipopolysaccharide moieties) itself, the major site of action for photodynamic disinfection. The higher proportion of monomeric methylene blue found in paraben containing photosensitizer compositions may also enhance the antimicrobial efficacy of photodynamic disinfection due to the increase singlet oxygen produced by the monomer. The paraben potentiation of photosensitizer compositions during photodynamic disinfection may allow for shorter illumination treatment durations (i.e., decreased applied energy doses) to achieve the same level of antimicrobial efficacy. It may also allow for the possibility of complete elimination of a pathogen such as *E. coli* from the desired treatment area even with the shorter treatment time, thereby avoiding recolonization of microbes and/or reinfection.

Example VI

The efficacy of photodynamic disinfection using the photosensitizer methylene blue was assessed in the presence and absence of parabens in order to determine whether there was a paraben potentiation effect against two common periopathogens: *Porphyromonas gingivalis* and *Prevotella intermedia*. These periopathogens have been positively implicated in the etiology of periodontal disease.

The in vitro experiment was conducted by growing *Porphyromonas gingivalis* (ATCC® 33277) and *Prevotella intermedia* (ATCC® 25611) under anaerobic conditions (e.g., using *Brucella agar* with Hemin and Vitamin K media) to log phase and preparing liquid planktonic cultures to a concentration of approximately $10^7$ CFU/ml. Subsequently, these planktonic cultures, were exposed to either a control containing a phosphate buffered saline solution or one of the following two compositions. Composition T contained the following ingredients: methylene blue at a concentration of about 0.01% w/v, in the isotonic buffered vehicle as described in Example II. Composition U contained the same ingredients as Composition T with the addition of methylparaben at a concentration of about 0.18% w/v and propylparaben at a concentration of about 0.02% w/v.

Preliminary experiments confirmed that exposure to Composition U containing methylparaben at a concentration of about 0.18% w/v and propylparaben at a concentration of about 0.02% w/v for up to 5 minutes in the absence of light did not result in any loss of bacterial viability. This result suggests that the paraben components did not exert acute antibacterial activity on their own under these parameters.

The planktonic cultures of the above-described organisms exposed to one of the above-described compositions (Composition T and U) were irradiated by a laser with a power output of about 100 mW at a wavelength of about 670 nm for durations of about 60 seconds at a power density of about 160 mW/cm$^2$ with an overall energy dose of about 9.6 J/cm$^2$.

After the above-described treatment(s), samples were serially diluted and plated on solid media for up to 5 days (thereby allowing colonies of bacteria to become visible in the non-irradiated phosphate buffered saline only controls). Plate counts for replicates of each experimental condition were averaged and back-calculated taking dilution into account to give data in CFU/ml. The data was presented as CFU/ml of surviving organisms after treatment(s), and kill rate was calculated as this value in experimental samples vs. the applicable non-irradiated phosphate buffered saline only control and expressed as both a log$_{10}$ and percentage reduction in bacterial viability ("B. viability").

Results of this study showed paraben potentiation in that the antimicrobial efficacy of photodynamic disinfection was enhanced in the presence of the parabens (Composition U) compared to using methylene blue alone (Composition T). For *Porphyromonas gingivalis* and compared to the controls, exposure to irradiated Composition T resulted in a 6.0 log$_{10}$ reduction in B. viability, and exposure to irradiated Composition U resulted in a 7.2 log$_{10}$ reduction in B. viability. Accordingly, exposure to Composition U resulted in a 1.2 log$_{10}$ (>10-fold) increase in bacterial killing as compared to Composition T. For *Prevotella intermedia*, exposure to irradiated Composition T resulted in a 3.5 log$_{10}$ reduction in B. viability, while exposure to irradiated Composition U resulted in a 5.1 log$_{10}$ reduction in B. viability. Accordingly, exposure to Composition U resulted in a 1.6 log$_{10}$ increase in bacterial killing as compared to Composition T. The results of this study using the periopathogens *Porphyromonas gingivalis* and *Prevotella intermedia* suggest a clear paraben potentiation effect on methylene blue photodynamic disinfection for these organisms.

What is claimed is:

1. A composition for photodynamic disinfection comprising: a phenothiazinium salt at a concentration ranges from about 0.001% w/v to about 1% w/v, and propylparaben at a concentration ranges from about 0.001% w/v to about 1 w/v, wherein (i) the composition is used for photodynamic disinfection of Gram-negative organism that is receptive to paraben potentiation and is located within a desired treatment area; and (ii) the composition provides the paraben potentiation against the Gram-negative organism during photodynamic disinfection of the Gram-negative organism by enhancing the antimicrobial efficacy of the phenothiazinium salt against the Gram-negative organism during the photodynamic disinfection.

2. The composition of claim 1 wherein the composition further includes a pharmaceutically acceptable carrier.

3. The composition of claim 1 wherein the composition further includes methylparaben.

4. The composition of claim 3 wherein concentration of the methylparaben ranges from about 0.001% w/v to about 1% w/v.

5. The composition of claim 3 wherein the photosensitizer is methylene blue at a concentration of about 0.01% w/v and the methylparaben is at a concentration of about (118% w/v and the propylparaben is at a concentration of about 0.02% w/v.

6. The composition of claim herein the photosensitizer is methylene blue.

7. The composition of claim 1 wherein the Gram-negative organism is selected from a group consisting of *Escherichia coli, Pseudomonas aeruginosa, Porphyromonas, Prevotella, Fusobacterium, Tannerella, Actinobacillus, Selenomonas, Eikenella, Campylobacter, Wolinella, Porphyromonas gingivalis, Prevotella intermedia*, and a combination thereof.

8. A method to enhance antimicrobial efficacy of a phenothiazinium salt against Gram-negative organism during photodynamic disinfection comprising:
 a. Applying a composition comprising (i) a phenothiazine salt at a concentration ranges from about 0.001% w/v to about 1% w/v; and (ii) propylparaben at a concentration ranges from 0.001% w/v to 1% w/v to a desired treatment area, and
 b. Applying light to the desired treatment area at a wavelength absorbed by the phenothiazinium salt so as to inhibit the Gram-negative organism located within the desired treatment area wherein (i) the Gram-negative organism is receptive to paraben potentiation; (ii) the composition provides the paraben potentiation against the Gram-negative organism by enhancing the antimicrobial efficacy of the phenothiazinium salt against the Gram-negative organism during the photodynamic disinfection.

9. The method of claim 8 wherein the composition further comprises methylparaben at a concentration ranges from about 0.001% w/v to about 1% w/v.

10. The method of claim 9 wherein (i) the methylparaben at a concentration of about 0.18% w/v; (ii) the phenothiazinium salt is methylene blue at a concentration of about 0.01% w/v; and (iii) the propylparaben is at a concentration of about 0.02% w/v; (iv) the wavelength ranges from about 600 nm to about 700 nm; and (v) energy dose of the light applied to the desired treatment area during the applying light to the desired treatment area step ranges from about 1 J/cm$^2$ to about 50 J/cm$^2$.

11. The method of claim 8 wherein the Gram-negative organism is *Porphyromonas gingivalis*.

12. The method of claim 8 wherein the Gram-negative organism is *Prevotella intermedia*.

13. The method of claim 8 wherein the Gram-negative organism is *Escherichia coli*.

* * * * *

UNITED STATES PATENT AND TRADEMARK OFFICE
CERTIFICATE OF CORRECTION

PATENT NO. : 8,703,050 B2  
APPLICATION NO. : 12/603861  
DATED : April 22, 2014  
INVENTOR(S) : Street et al.

Page 1 of 1

It is certified that error appears in the above-identified patent and that said Letters Patent is hereby corrected as shown below:

On Title Page 2, References Cited, OTHER PUBLICATIONS, Line 6
Delete "J. Breslin:" and insert --J. Bredin,--

In the Claims

Column 11, Claim 1, Line 40, delete "to about 1 w/v," and insert --to about 1% w/v,--
Column 12, Claim 5, Line 6, delete "about (118% w/v" and insert --about 0.18% w/v--
Column 12, Claim 6, Line 9, delete "claim herein" and insert --claim 1 wherein--
Column 12, Claim 8, Line 24, delete "area," and insert --area;--

Signed and Sealed this  
Twenty-ninth Day of July, 2014

Michelle K. Lee  
*Deputy Director of the United States Patent and Trademark Office*